United States Patent

Lantzsch et al.

[11] Patent Number: 4,582,856
[45] Date of Patent: Apr. 15, 1986

[54] PESTICIDAL 2,2-DIMETHYL-3-(2-HALOGENO-VINYL)-CYCLOPROPANECARBOXYLIC ACID ESTERS

[75] Inventors: Reinhard Lantzsch, Leverkusen; Benedikt Becker, Mettmann; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 591,661

[22] Filed: Mar. 20, 1984

[30] Foreign Application Priority Data

Apr. 7, 1983 [DE] Fed. Rep. of Germany ....... 3312543

[51] Int. Cl.$^4$ ............... A01N 53/00; C07C 69/743; C07C 121/75
[52] U.S. Cl. ............... 514/521; 260/544 L; 260/544 D; 260/544 S; 514/277; 514/345; 514/351; 514/357; 514/531; 546/300; 546/302; 546/330; 546/342; 560/8; 560/18; 560/65; 560/124; 562/405; 562/432; 562/474; 562/502; 558/407
[58] Field of Search .......... 260/465 D, 544 L, 544 D, 260/544 S; 560/8, 18, 64, 65, 124; 562/405, 432, 474, 506; 514/277, 345, 351, 357, 521, 531; 546/300, 302, 330, 342

[56] References Cited

U.S. PATENT DOCUMENTS 4,183,942 1/1980 Engel .................. 260/465 D X
4,200,644 4/1980 Engel .................. 260/465 D X
4,279,923 7/1981 Fuchs et al. ................ 424/304

FOREIGN PATENT DOCUMENTS 0009709 4/1980 European Pat. Off. .
0095047 11/1983 European Pat. Off. .

Primary Examiner—Dolph H. Torrence
Attorney, Agent, or Firm—Sprung Horn Kramer & Woods

[57] ABSTRACT

Pesticidally active 2,2-dimethyl-3-(2-halogeno-vinyl)-cyclopropanecarboxylic acid esters of the formula

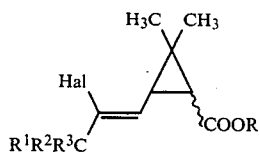

in which
$R^1$ and $R^2$ are identical or different and represent alkyl or halogenoalkyl,
$R^3$ represents alkyl or the grouping $-(CH_2)-_nR^4$,
in which
n represent 0 or 1 and
$R^4$ represents halogenoalkyl, optionally substituted aryl or the grouping $-XR^5$,
in which
X represents oxygen or sulphur and
$R^5$ represents alkyl, halogenoalkyl, optionally substituted aryl or optionally substituted aralkyl,
Hal represents fluorine, chlorine or bromine and
R represents an alcohol radical which can be used in the case of pyrethroids.

Intermediates carrying an acid, acid chloride or alkyl ester group in place of —COOR are also new.

14 Claims, No Drawings

PESTICIDAL 2,2-DIMETHYL-3-(2-HALOGENO-VINYL)-CYCLOPROPANECARBOXYLIC ACID ESTERS

The present invention relates to new 2,2-dimethyl-3-(2-halogen-vinyl)-cyclopropanecarboxylic acid esters, a process for their preparation and their use as agents for combating pests, in particular as insecticides and acaricides.

It is already known that 2,2-dimethyl-3-vinylcyclopropanecarboxylic acid esters, such as, for example, 3-phenoxy-benzyl 3-(2,2-dichlorovinyl)-2,2-dimethyl-cyclopropanecarboxylate, 3-phenoxy-α-cyano-benzyl 3-(2,2-dichloro-vinyl)-2,2-dimethyl-cyclopropanecarboxylate, 4-fluoro-3-phenoxy-α-cyano-benzyl 2,2-dimethyl-3-hex-1-enecyclopropanecarboxylate and 4-fluoro-3-phenoxy-α-cyanobenzyl 3-[2-chloro-2-(4-chlorophenyl)]-2,2-dimethyl-cyclopropanecarboxylate, have an insecticidal and acaricidal action (DE-OS (German Published Specification) No. 2,326,077, U.S. Pat. No. 4,376,786 and U.S. Ser. No. 135,070, filed Mar. 28, 1980, pending).

However, the action of these compounds is not completely satisfactory when low concentrations are applied.

New 2,2-dimethyl-3-(2-halogeno-vinyl)-cyclopropanecarboxylic acid esters of the formula (I)

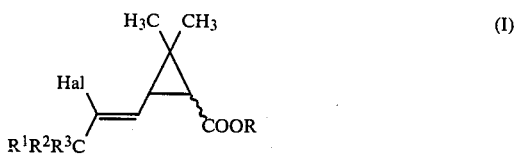

in which $R^1$ and $R^2$ are identical or different and represent alkyl or halogenoalkyl, $R^3$ represents alkyl or the grouping $-(CH_2)_nR^4$, in which n represents 0 or 1 and $R^4$ represents halogenoalkyl, optionally substituted aryl or the grouping $-XR^5$, in which X represents oxygen or sulphur and $R^5$ represents alkyl, halogenoalkyl, optionally substituted aryl or optionally substituted aralkyl, Hal represents fluorine, chlorine or bromine and R represents an alcohol radical which can be used in the case of pyrethroids.

The general formula (I) includes the possible stereoisomers and optical isomers and mixtures thereof.

The new compounds of the formula I are obtained when 2,2-dimethyl-3-(2-halogeno-vinyl)-cyclopropanecarboxylic acids of the formula (II)

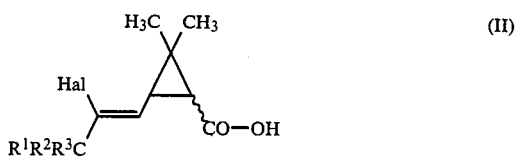

in which $R^1$, $R^2$, $R^3$ and Hal have the abovementioned meanings, or reactive derivatives thereof, are reacted with alcohols of the formula (III)

$$R-OH \quad (III)$$

in which R has the abovementioned meaning, or with reactive derivatives thereof, if appropriate in the presence of acid acceptors, if appropriate in the presence of catalysts and if appropriate in the presence of diluents.

The new 2,2-dimethyl-3-(2-halogeno-vinyl)-cyclopropanecarboxylic acid esters are distinguished by a powerful pesticidal, in particular insecticidal and acaricidal, action and a low toxicity to fish.

Surprisingly, the compounds of the formula (I) according to the invention exhibit a more powerful insecticidal and acaricidal action than the 2,2-dimethyl-3-vinyl-cyclopropanecarboxylic acid esters already mentioned, such as, for example, 3-phenoxy-benzyl 3-(2,2-dichlorovinyl)-2,2-dimethyl-cyclopropanecarboxylate, 3-phenoxy-α-cyano-benzyl 3-(2,2 dichloro-vinyl)-2,2-dimethyl-cyclopropanecarboxylate, 4-fluoro-3-phenoxy-α-cyano-benzyl 2,2-dimethyl-3-hex-1-ene-cyclopropanecarboxylate and 4-fluoro-3-phenoxy-α-cyano-benzyl 3-[2-chloro-2-(4-chlorophenyl)]-2,2-dimethyl-cyclopropanecarboxylate.

The invention preferably relates to compounds of the formula (I) in which $R^1$ and $R^2$ are identical or different and represent alkyl with 1 to 6 carbon atoms or halogenoalkyl with 1 to 4 carbon atoms in the alkyl part and 1 to 5 identical or different halogen atoms, such as fluorine, chlorine and/or bromine, $R^3$ represents alkyl with 1 to 12 carbon atoms or the grouping $-(CH_2)_nR^4$, in which n represents 0 or 1 and $R^4$ represents halogenoalkyl with 1 to 4 carbon atoms in the alkyl part and 1 to 5 identical or different halogen atoms, optionally substituted aryl with 6 to 10 carbon atoms, such as naphthyl or phenyl, preferably phenyl, or the grouping $XR^5$, in which X represents oxygen or sulphur and $R^5$ represents alkyl with 1 to 6 carbon atoms, halogenoalkyl with 1 to 4 carbon atoms and 1 to 5 identical or different halogen atoms or optionally substituted aryl with 6 to 10 carbon atoms or aralkyl with 6 to 10 carbon atoms in the aryl part and 1 or 2 carbon atoms in the alkyl part. Preferred possible substituents on the aryl are: alkyl, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms and/or halogen, such as fluorine, chlorine and/or bromine;

Hal represents fluorine, chlorine or bromine and

R represents a radical $-CHR^6R^7$, in which $R^6$ represents hydrogen, cyano or optionally substituted alkenyl or alkinyl with 2 to 4 carbon atoms and $R^7$ represents phenyl or 2-pyridinyl, each of which is optionally substituted by halogen and/or phenoxy which is substituted by halogen, alkyl or halogenoalkyl.

Particularly preferred compounds of the formula (I) are those in which $R^1$ and $R^2$ are identical or different and represent alkyl with 1 to 4 carbon atoms or halogenoalkyl with 1 or 2 carbon atoms in the alkyl part and 1 to 3 identical or different halogen atoms, such as fluorine and/or chlorine, $R^3$ represents alkyl with 1 to 6 carbon atoms or the grouping —$(CH_2)_nR^4$,
in which
n represents 0 or 1 and
$R^4$ represents halogenoalkyl with 1 to 4 carbon atoms in the alkyl part and 1 to 5 identical or different halogen atoms, optionally substituted phenyl or the grouping $XR^5$,
in which
X represents oxygen or sulphur and
$R^5$ represents alkyl with 1 to 4 carbon atoms, halogenoalkyl with 1 to 4 carbon atoms and 1 to 5 identical or different halogen atoms or optionally substituted phenyl or phenylalkyl with 1 or 2 carbon atoms in the alkyl part.

Possible substituents on the phenyl are: fluorine, chlorine, methyl, tert.-butyl, methoxy, methylthio, trifluoromethyl and/or trifluoromethoxy.

Hal represents chlorine or bromine and
R represents a radical —$CHR^6R^7$,
in which
$R^6$ represents hydrogen or cyano and
$R^7$ represents 3-phenoxy-phenyl, 4-fluoro-3-phenoxyphenyl, 3-(4-fluoro-phenoxy)-phenyl, 4-fluoro-3-(4-fluoro-phenoxy)-phenyl, pentafluorophenyl or 6-phenoxy-2-pyridyl.

Very particularly preferred compounds of the formula (I) are those in which
$R^1$ and $R^2$ are identical or different and represent methyl, ethyl, chloromethyl, chloroethyl, fluoromethyl or fluoroethyl,
$R^3$ represents methyl, ethyl, n-propyl, i-propyl, n-butyl, n-pentyl, n-hexyl or the grouping —$(CH_2)_nR^4$,
in which
n represents 0 or 1,
$R^4$ represents chloromethyl, fluoromethyl, phenyl which is optionally substituted by fluorine, chlorine, bromine, methyl, methoxy, trifluoromethyl or trifluoromethoxy, or the grouping $XR^5$,
in which
X represents oxygen or sulphur and
$R^5$ represents methyl, ethyl, trifluoromethyl, trichloromethyl, or phenyl or benzyl which is optionally substituted by fluorine, chlorine, bromine, methyl, methoxy, trifluoromethyl and/or trifluoromethoxy,
Hal represents chlorine and
R represents a radical —$CHR^6R^7$,
in which
$R^6$ represents hydrogen or cyano and
$R^7$ represents 3-phenoxy-phenyl, 4-fluoro-3-phenoxyphenyl or pentafluorophenyl.

In a preferred variant (a) of the preparation process for the compounds of the formula (I), 2,2-dimethyl-3-(2-halogeno-vinyl)-cyclopropanecarboxylic acid chlorides of the formula (IIa)

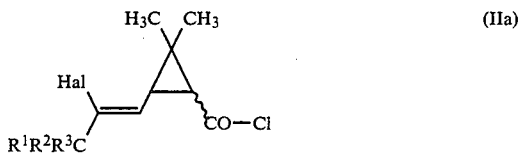

in which $R^1$, $R^2$, $R^3$ and Hal have the abovementioned meanings, are reacted with alcohols of the formula (III) (above) in the presence of acid acceptors, using diluents.

In a further preferred variant (b)-for the preparation of compounds of the formula (I) in which $R^6$ represents cyano-2,2-dimethyl-3-(2-halogeno-vinyl)-cyclopropanecarboxylic acid chlorides of the formula (IIa) are reacted with
(α) corresponding aldehydes of the formula (IV)

in which $R^7$ has the abovementioned meaning, and at least the equimolar amount of an alkali metal cyanide (sodium cyanide or potassium cyanide) in the presence of water and water-immiscible organic solvents and if appropriate in the presence of a catalyst; or
(β) cyanohydrins of the formula (V)

in which $R^7$ has the abovementioned meaning, in the presence of acid acceptors, using diluents.

If, for example, 3-(2-chloro-3,3-dimethyl-1-butenyl)-2,2-dimethyl-cyclopropanecarboxylic acid chloride and 3-phenoxy-benzyl alcohol are used as starting substances in process variant (a), the reaction can be outlined by the following equation:

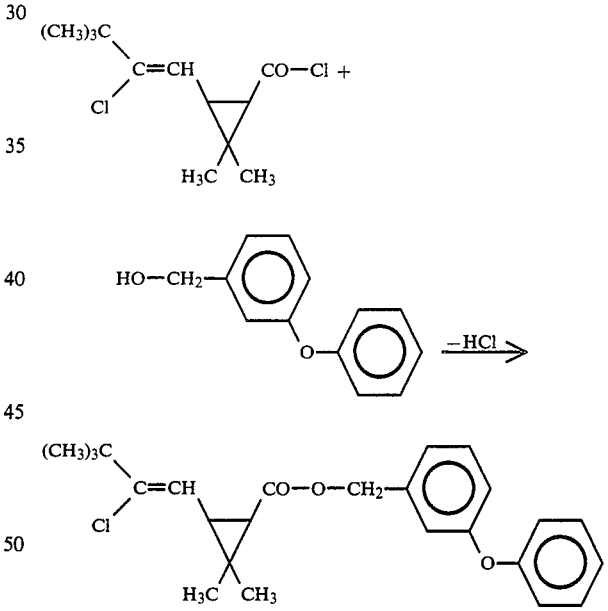

If 3-(2-chloro-3,3-dimethyl-1-butenyl)-2,2-dimethyl-cyclopropanecarboxylic acid chloride, sodium cyanide and 3-phenoxy-benzaldehyde are used as starting substances in process variant (b/α), the course of the reaction can be outlined by the following equation:

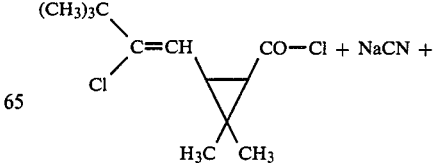

-continued

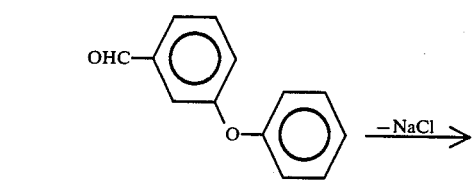

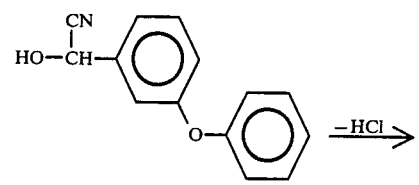

If 3-(2-chloro-3,3-dimethyl-1-butenyl)-2,2-dimethyl-cyclopropanecarboxylic acid chloride and 3-phenoxy-α-cyano-benzaldehyde are used as starting substances in process variant (b/β), the course of the reaction can be outlined by the following equation:

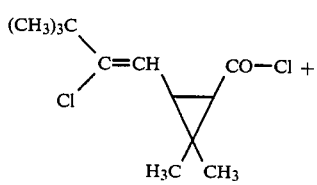

Formula (II) provides a definition of the 2,2-dimethyl-3-(2-halogeno-vinyl)-cyclopropanecarboxylic acids to be used as starting substances, and formula (IIa) provides a definition of the corresponding acid chlorides.

In these formulae, $R^1$, $R^2$, $R^3$ and Hal preferably or in particular have the same meanings as have been mentioned as preferred or as particularly preferred in the definition of the corresponding radical in formula (I).

Examples which may be mentioned of the compounds of the formula (II) and the corresponding acid chlorides of the formula (IIa) are:

TABLE 1

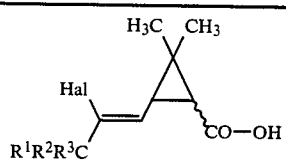
(II)

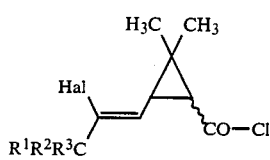
(IIa)

Hal = chlorine, fluorine or bromine

| $R^1$ | $R^2$ | $R^3$ | $R^1$ | $R^2$ | $R^3$ |
|---|---|---|---|---|---|
| CH₃ | CH₃ | —O—⟨C₆H₄⟩—Cl | CH₃ | CH₃ | —CH₂OCH₃ |
| CH₃ | CH₃ | —CH₂—O—⟨C₆H₄⟩—Cl | CH₃ | CH₃ | —CH₂—S—⟨C₆H₅⟩ |
| CH₃ | CH₃ | —⟨C₆H₅⟩ | CH₃ | CH₃ | —CH₂—S—⟨C₆H₄⟩—F |
| CH₃ | CH₃ | CH₃ | CH₃ | CH₃ | —CH₂—O—⟨C₆H₄⟩—CH₃ |

TABLE 1-continued $$\begin{array}{c} \text{H}_3\text{C} \quad \text{CH}_3 \\ \text{Hal} \\ \diagdown \\ \text{R}^1\text{R}^2\text{R}^3\text{C} \quad \text{CO—OH} \end{array} \quad (II)$$

$$\begin{array}{c} \text{H}_3\text{C} \quad \text{CH}_3 \\ \text{Hal} \\ \diagdown \\ \text{R}^1\text{R}^2\text{R}^3\text{C} \quad \text{CO—Cl} \end{array} \quad (IIa)$$

Hal = chlorine, fluorine or bromine

| $R^1$ | $R^2$ | $R^3$ | $R^1$ | $R^2$ | $R^3$ |
|---|---|---|---|---|---|
| CH₃ | CH₃ | CH₂Cl | CH₃ | CH₃ | —CH₂—O—C₆H₄—F |
| CH₃ | CH₃ | CH₂F | | | |
| CH₃ | CH₃ | —C₆H₄—Cl | CH₃ | CH₃ | —CH₂—C₆H₄—F |
| CH₃ | CH₃ | —SCF₃ | CH₃ | CH₃ | —CH₂—C₆H₄—Cl |
| CH₃ | CH₃ | —CH₂—S—C₆H₄—Cl | CH₃ | CH₃ | —CH₂—C₆H₄—Cl (o) |
| CH₃ | CH₃ | —CH₂OC₂H₅ | CH₃ | CH₃ | —CH₂—C₆H₃(Cl)₂ (3,4) |
| CH₃ | CH₃ | —SCCl₃ | | | |
| CH₃ | CH₂Cl | CH₃ | CH₃ | CH₃ | C₂H₅ |
| CH₃ | CH₂Cl | CH₂Cl | CH₃ | CH₃ | C₃H₇—n |
| CH₃ | CH₂Cl | CH₂F | CH₃ | CH₃ | C₃H₇—i |
| CH₃ | CH₂F | CH₃ | CH₃ | CH₃ | C₆H₉—n |
| CH₃ | CH₂F | CH₂F | CH₃ | CH₃ | C₅H₁₁—n |
| CH₃ | CH₂F | —SCF₃ | CH₃ | CH₃ | C₆H₁₃—n |
| CH₃ | CH₃ | —CH₂—C₆H₄—OCF₃ | CH₃ | CH₃ | —CH₂—CH₂F |
| CH₃ | CH₃ | —CH₂—C₆H₃(Cl)₂ | | | |

The 2,2-dimethyl-3-(2-halogeno-vinyl)-cyclopropanecarboxylic acid chlorides of the formula (IIa) are new, but they can be prepared by customary methods from the corresponding carboxylic acids of the formula (II), by reaction with a chlorinating agent, such as, for example, thionyl chloride, if appropriate using a diluent, such as, for example, carbon tetrachloride, at temperatures between 10° C. and 100° C.

The 2,2-dimethyl-3-(2-halogeno-vinyl)-cyclopropanecarboxylic acid chlorides of the formula (IIa) are also new. They are obtained, for example, by a process in which vinyl-aldehydes of the formula (VI)

in which $R^1$, $R^2$, $R^3$ and Hal have the abovementioned meanings, are reacted with methyl-butan-3-one of the formula (VII)

in the presence of hydrogen halide acids, the 4,4 dimethyl-3-halogeno-1-hexen-5-ones which can thereby be obtained, of the formula (VIII),

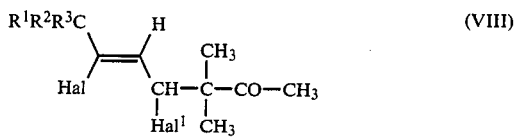

in which
$R^1$, $R^2$, $R^3$ and Hal have the abovementioned meanings and
$Hal^1$ represents chlorine or bromine, are halogenated and the compounds which can thereby be obtained, of the formula (IX),

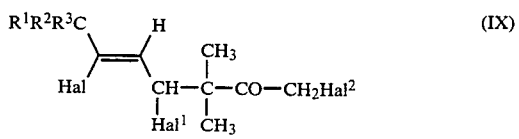

in which
$R^1$, $R^2$, $R^3$, Hal and $Hal^1$ have the abovementioned meanings and
$Hal^2$ represents chlorine or bromine, are reacted with bases of the formula (X)

MO—Z  (X)

in which
M represents one equivalent of an alkali metal ion or alkaline earth metal ion and
Z represents hydrogen or $C_1$-$C_4$-alkyl.

The general formula (VI) provides a definition of the vinyl-aldehydes to be used as starting substances. Preferably, or particularly preferably, in these formulae, $R^1$, $R^2$, $R^3$ and Hal represent those radicals which have already been mentioned as preferred or as particularly preferred in the definition of $R^1$, $R^2$, $R^3$ and Hal in formula (I).

Vinyl-aldehydes of the formula (VI) to be used as starting substances are known and can be prepared by known methods (for example Zeitschrift für Chemie 1976 16, page 337; and 1973, 13, page 97; and Chem. Ber. 98, page 3,554.

The compound 2-methyl-butan-1-one of the formula (VII) also to be used as starting substances is known.

The reaction is carried out in the presence of at least equimolar amounts of hydrogen chloride or hydrogen bromide, and if appropriate using diluents. Possible diluents are all the solvents which are inert towards hydrogen chloride or hydrogen bromide. The reaction is preferably carried out without a solvent, at temperatures between 0° C. and 25° C. (in this context, compare German Patent Application P 32 31 814, which has not been published).

If the reaction is carried out without a diluent, the 2-methyl-3-butanone can be used in excess. 1 to 10, preferably 1 to 4, equivalents of ketone are usually employed per equivalent of vinyl-aldehyde of the formula (VI).

The 4,4-dimethyl-3-halogen-1-hexen-5-ones of the formula (VIII) which can be obtained in the reaction of the vinyl-aldehydes of the formula (VI) with the methylbutanone of the formula (VII) are new. They can be isolated and purified, or can be subsequently reacted immediately in the next stage, without further purification.

Compounds of the formula (IX) are obtained by halogenating compounds of the formula (VIII) (above).

Formula (VIII) provides a general definition of the 4,4-dimethyl-3-halogen-1-hexen-5-ones. Preferably or particularly preferably, in this formula, $R^1$, $R^2$, $R^3$ and Hal represent those radicals which have already been mentioned as preferred or as particularly preferred in the definition of $R^1$, $R^2$, $R^3$ and Hal in formula (I). $Hal^1$ in formula (VIII) represents chlorine or bromine.

Possible halogenating agents are chlorine, bromine and sulphuryl chloride.

The reaction is usually carried out in an inert diluent. Possible inert diluents are, for example, chlorohydrocarbons, such as, for example, chloroform.

The reaction temperature should not exceed 40° C., and the reaction is preferably carried out at between −10° C. and +25° C.

One equivalent of halogenating agent is usually employed per mole of the compound of the formula VIII. However, an excess of compounds of the formula VIII can also be used.

The compounds of the formula (IX) which can be obtained in the halogenation of the compounds of the formula (VIII) are new. They can be isolated and purified, or can subsequently be reacted immediately in the next stage, without further purification.

The 2,2-dimethyl-3-(2-halogeno-vinyl)-cyclopropanecarboxylic acids of the formula (II) (above) are obtained by reacting compounds of the formula (IX) with bases of the formula (X).

Formulae (IX) and (X) provide general definitions of the starting substances to be used in the process.

Preferably or particularly preferably, in these formulae, $R^1$, $R^2$, $R^3$ and Hal represent those radicals which have already been mentioned as preferred or as particularly preferred in the definition of $R^1$, $R^2$, $R^3$ and Hal in formula (I). $Hal^1$ and $Hal^2$ represent chlorine or bromine, M represents one molar equivalent of an alkali metal ion or alkaline earth metal ion and Z represents hydrogen or $C_1$-$C_4$-alkyl.

Specific example of bases which may be mentioned are: sodium hydroxide, potassium hydroxide, calcium hydroxide, sodium methylate, sodium ethylate, sodium butylate and potassium tert.-butylate.

If the hydroxides are used, the reaction is preferably carried out in water and/or an inert diluent. Examples of possible inert diluents are alcohols, such as methanol, ethanol and t.-butanol, ethers, such as dioxane, tetrahydrofuran and dimethoxyethane, or ketones, such as acetone, and dimethylformamide. However, water-immiscible solvents, such as methylene chloride, petroleum ether, cyclohexane, toluene or chlorobenzene, can also be used, if necessary in the presence of a phase transfer catalyst.

If the alcoholates are used, the reaction is most advantageously carried out in the corresponding alcohols.

The reaction temperatures can be varied within a substantial range. In general, the reaction is carried out between 0° C. and 150° C., preferably between 20° C. and 100° C.

At least 2 equivalents of bases (X) must be employed per mole of starting substance of the formula (IX). An excess of base of up to 10 equivalents is usually advantageous. In the preparation of the acids (X=H), the reaction mixture is worked up by extraction in the alkaline range (in order to remove impurities) and, after acidification of the aqueous phase, by renewed extraction. In the preparation of esters, purification is carried out by distillation. The mixture is first diluted with water, rendered neutral and extracted (in this context, compare the preparation examples).

The general formula (III) and (V) provide definitions of the alcohols and cyanohydrins also to be used as starting substances—for the preparation of the compounds of the formula (I). In these formulae (III) and (V), R and $R^7$ preferably or in particular represent those radicals which have already been mentioned as preferred or as particularly preferred in the definition of R and $R^7$ in formula (I).

Examples which may be mentioned of the alcohols of the formula (III) and cyanohydrins of the formula (V) are: 6-phenoxy-2-pyridylmethanol, α-cyano-6-phenoxy-2-pyridylmethanol, 4-fluoro-3-phenoxy-benzyl alcohol, 3-phenoxy-benzyl alcohol, α-cyano-4-fluoro-3-phenoxy-benzyl alcohol, α-cyano-3-phenoxy-benzyl alcohol, 4-fluoro-3-(4-chloro-phenoxy)-benzyl alcohol, 4-fluoro-3-(4-bromo-phenoxy)-benzyl alcohol, pentafluoro benzyl alcohol, 4-fluoro-3-(4-fluoro-phenoxy)-benzyl alcohol, α-cyano-4-fluoro-3-(4-fluoro-phenoxy)-benzyl alcohol, 4-fluoro-3-(3-fluoro-phenoxy)-benzyl alcohol and α-cyano-4-fluoro-3-(3-fluoro-phenoxy)-benzyl alcohol.

The compounds of the formula (III) are already known (compare U.S. Pat. No. 4,163,787, U.S. Pat. No. 3,835,176, DE-OS (German Published Specification) No. 2,709,264, DE-OS (German Published Specification) No. 3,103,325, DE-OS (German Published Specification) No. 2,739,854, DE-OS (German Published Specification) No. 2,658,074 and J. Chem. Soc. 1961, 808–817).

Formula (IV) provides a definition of the aldehydes which can be used as starting substances. In this formula, $R^7$ has the same preferred or particularly preferred meaning as the corresponding radicals in formula (I).

Examples which may be mentioned of the aldehydes of the formula (IV) are: 6-phenoxy-2-pyridyl-carbaldehyde, α-cyano-6-phenoxy-2-pyridyl-carbaldehyde, 4-fluoro-3-phenoxy-benzaldehyde, 3-phenoxy-benzaldehyde, α-cyano-4-fluoro-3-phenoxy-benzaldehyde, α-cyano-3-phenoxy-benzaldehyde, 3-(4-chloro-phenoxy)-4-fluoro-benzaldehyde, 3-(4-bromo-phenoxy)-4-fluoro-benzaldehyde, 4-fluoro-3-(4-fluoro-phenoxy)-benzaldehyde, α-cyano-4-fluoro-3-(4-fluoro-phenoxy)-benzaldehyde, 4-fluoro-3-(3-fluorophenoxy)-benzaldehyde and α-cyano-4-fluoro-3-(3-fluorophenoxy)-benzaldehyde.

The compounds of the formula (IV) are already known (compare U.S. Pat. No. 4,163,787, U.S. Pat. No. 3,835,176, U.S. Pat. No. 4,261,920, U.S. Ser. No 339,016, filed Jan. 2, 1982, pending and U.S. Pat. Nos. 4,199,596 and 4,183,050).

All variants of the process for the preparation of the new compounds of the formula (I) are preferably carried out using diluents. Possible diluents are virtually all the inert organic solvents. These include, in particular, aliphatic and aromatic, optionally halogenated hydrocarbons, such as pentane, hexane, heptane, cyclohexane, petroleum, ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionnitrile, amides, such as, for example, dimethylformamide, dimethylacetamide and N-methylpyrrolidone, and dimethylsulphoxide, tetramethylenesulphone and hexamethylphosphoric acid triamide.

Variants (a) and (b/β) of the process according to the invention are preferably carried out in the presence of acid acceptors. The customary acid-binding agents can be used as acid acceptors. Alkali metal carbonates and alcoholates, such as sodium carbonate, potassium carbonate, sodium ethylate and methylate and potassium ethylate and methylate, and furthermore aliphatic, aromatic or heterocyclic amines, for example triethylamine, trimethylamine, dimethylaniline, dimethylbenzylamine, pyridine, diazabicyclooctane, diazabicyclononene and diazabicycloundecene, have proved particularly suitable.

Variant (b/β) of the process according to the invention is carried out in the presence of water and one of the abovementioned organic solvents, as long as this is water-immiscible. The abovementioned hydrocarbons are particularly suitable for this.

Compounds which are suitable for transferring anions from water into organic solvents are preferably suitable as catalysts in process variant (b/α). Examples of these compounds are benzyl-triethyl-ammonium bisulphate, tetrabutylammonium bromide and methyl-tri-octylammonium chloride (Aliquat 336 ®).

The reaction temperature can be varied within a substantial range in all process variants. In general, the reaction is carried out between 0° C. and 100° C., preferably at 10° C. to 50° C.

The process according to the invention is in general carried out under normal pressure. The starting substances are usually employed in equimolar amounts for carrying out the process according to the invention. An excess of one or the other of the reaction components provides no substantial advantages. The starting substances are brought together in suitable diluents and stirred until the reaction has ended—if necessary after addition of an acid acceptor and/or a catalyst.

Working up can be carried out by customary methods, for example by a procedure in which, if appropriate, the reaction mixture is diluted with water and/or a water immiscible organic solvent, such as, for example, toluene, the organic phase is separated off, washed with water, dried and filtered and the solvent is carefully distilled off from the filtrate under reduced pressure and at moderately elevated temperature ("incipient distillation").

As already mentioned, the 2,2-dimethyl-3-(2-halogeno-vinyl)-cyclopropanecarboxylic acid esters are distinguished by a powerful insecticidal and acaricidal activity.

They can be used in agriculture and forestry against insects and mites which damage plants, and in the veterinary medicine sector against ectoparasites.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example *Lepisma saccharina.* From the order of the Collembola, for example, *Onychiurus armatus.* From the order to the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria melllonella, Tineola bisselliella, Tinea pellionella, Hofmannophila pseudospretella, cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedea spp., Anopheles spp., Culex spp., *Drosophila melanogaster,* Musca spp., Fannia spp., *Calliphora erythrocephala,* Lucilia spp., Chrysomia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, Xenopsylla cheopis and Ceratophyllus spp.. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The new active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compound with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquid which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohols ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nemtaticies, fungicies, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of livestock husbandry and animal breeding, it being possible to achieve better results, for example a higher milk yield, higher weight, better animal skin, longer life and the like, by combating the pests.

The active compounds according to the invention are used in a known manner in these fields, such as by external use in the form of, for example, dipping, spraying, pouring on and spotting on, and powdering, and by oral administration, for example via the feed or drinking water, in the form of, for example, tablets, capsules, drinks or granules.

PREPARATION EXAMPLES

Example 1 :

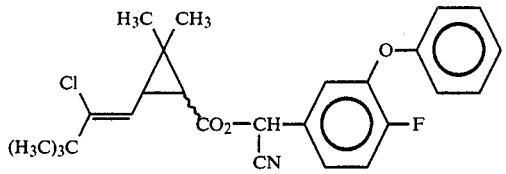

17.6 g (0.07 mole) of cis/trans-3-(Z-2-chloro-3,3-dimethyl-1-butenyl)-2,2-dimethyl-cyclopropane-1-carboxylic acid chloride and 17.17 g (0.07 mole) of α-cyano-4-fluoro-3-phenoxybenzyl alcohol are initially introduced into 300 ml of toluene. 5.58 g (0.07 mole) of pyridine are then added dropwise at 20° C. and the mixture is subsequently stirred for 16 hours. It is then washed with water, sodium bicarbonate solution and water. The organic phase is separated off, dried over sodium sulphate and concentrated. Last residues of solvent are removed by "incipient distillation".

31.8 g (99.7% of theory) of α-cyano-4-fluoro-3-phenoxy-benzyl cis/trans-3-(Z-2-chloro-3,3-dimethyl-1-butenyl)-2,2-dimethyl-cyclopropane-1-carboxylate are obtained as an almost colorless oil of refractive index $N_D^{20}$: 1.539.

The other compounds of the formula (I) are obtained analogously to Example 1 or according to process variants (a), (b/α) and (b/β):

TABLE 2

| Example No. | Formula | Refractive index $n_D^{20}$ |
|---|---|---|
| 2 | H₃C CH₃ / Cl / (H₃C)₃C / COO—CH(CN)—C₆H₄—O—C₆H₅ / Z cis/trans | 1.545 |
| 3 | H₃C CH₃ / Cl / (H₃C)₃C / COOCH₂—C₆F₅ / Z cis/trans | 1.479 |

TABLE 2-continued

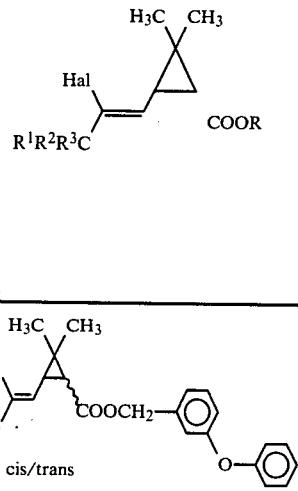

| Example No. | Formula | Refractive index $n_D^{20}$ |
|---|---|---|
| 4 | Cl<br>H₃C  CH₃<br>(H₃C)₃C–C=...–COOCH₂–C₆H₄–O–C₆H₅<br>Z cis/trans | |
| 5 | H₃C CH₃, Cl, (H₃C)₂C(CH₂F)–, COO–CH(CN)–C₆H₄–O–C₆H₅<br>Z cis/trans | 1.542 |
| 6 | H₃C CH₃, Cl, (H₃C)₂C(CH₂F)–, COO–CH(CN)–C₆H₃(F)–O–C₆H₅<br>Z cis/trans | 1.535 |
| 7 | H₃C CH₃, Cl, (H₃C)₂C(CH₂F)–, COO–CH(CN)–C₆H₃(F)–O–C₆H₅<br>Z trans | 1.536 |
| 8 | H₃C CH₃, Cl, (H₃C)₂C(CH₂Cl)–, COO–CH(CN)–C₆H₃(F)–O–C₆H₅<br>Z cis/trans | 1.535 |
| 9 | H₃C CH₃, Cl, (H₃C)₃C–, COO–CH(CN)–C₆H₃(F)–O–C₆H₅<br>Z trans | 1.536 |

Preparation of the starting substances of the formula (VI)

Example (VI-1)

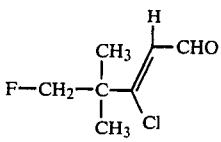

307 g (2 moles) of phosphorus oxychloride are added dropwise to 175.2 g (2.4 moles) of dimethylformamide at about 10° C., and 94.4 g (0.8 mole) of 4-fluoro-3,3-dimethyl-2-butanone are then added dropwise at 20° C. After 30 minutes, the temperature increases slowly to 50° C. After the mixture has been subsequently stirred for 3 hours, it is poured onto 2.5 liters of ice-water and extracted three times with ether. The aqueous phase is adjusted to pH 5.6 with sodium acetate and is extracted again three times with ether. These extracts are washed with sodium bicarbonate solution and then with water, dried over sodium sulphate and concentrated.

After distillation, 68.8 g of 5-fluoro-3-chloro-4,4-dimethyl-2-penten-1-al of boiling point 89° C. to 91° C./14 mbar are obtained.

Example (VI-2)

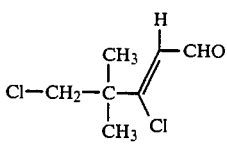

276.5 g (1.8 moles) of phosphorus oxychloride are added dropwise to 157.7 g (2.16 L moles) of dimethylformamide at about 10° C., and 97.5 g (0.72 mole) of 4-chloro-3,3-dimethyl-2-butanone are then added dropwise at 20° C. When the dropwise addition has ended, the reaction mixture is no longer cooled, so that the temperature rises to about 35° C. After the mixture has been subsequently stirred for 3 hours, it is poured onto 2 liters of icewater. Working up is effected as in Example (VI-1).

23.1 g of 3,5-dichloro-4,4-dimethyl-2-penten-1-al of boiling point 112° C./14 mbar are obtained.

The remaining starting substances of the formula (VI) are obtained analogously to Example (VI-1) and (VI-2).

Preparation of the starting substances of the formula (VIII)

Example (VIII-1)

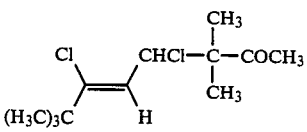

A mixture of 29.3 g (0.2 mole) of 3-chloro-4,4-dimethyl-2-pentenal and 34.4 g (0.4 mole) of methyl isopropyl ketone is saturated with hydrogen chloride at 10° C. and subsequently stirred at 20° C. for 12 hours. The solution is washed with water, neutralized with sodium carbonate and extracted three times with methylene chloride.

The combined organic phases are washed with water, dried over sodium sulphate and concentrated.

45.4 g (90.4% of theory) of 4,6-dichloro-3,3,7,7-tetramethyl-5-octen-2-one of boiling point b.p. 120° C./0.1 mbar are obtained.

The remaining compounds of the formula (VIII) are obtained analogously to Example (VIII-1), such as, for example:

Example (VIII-2)

Cl\C(CH₂F)(H₃C)₂C=CH—CHCl—C(CH₃)₂—COCH₃   Boiling point 110° C./0.1 mbar

Example (VIII-3)

Cl\C(CH₂Cl)(H₃C)₂C=CH—CHCl—C(CH₃)₂—CO—CH₃   Boiling point 130° C./0.1 mbar

Starting substances of the formula (IX)

Example (IX-1)

Cl\C(H₃C)₃C=CH—CHCl—C(CH₃)₂—CO—CH₂Br.

20 g (0.0796 mole) of 4,6-dichloro-3,3,7,7-tetramethyl-5-octen-2-one are dissolved in 350 ml of chloroform, and 12.74 g (0.0796 mole) of bromine are added at 20° C. to 25° C. After about 15 minutes, hydrogen bromide is evolved. The solution becomes discolored after about 45 minutes and is concentrated.

26.3 g of crude 1-bromo-4,6-dichloro-3,3,7,7-tetramethyl-5-octen-2-one, the structure of which is confirmed by the ¹H-NMR spectrum, are obtained. It is employed directly in the next stage.

The remaining compounds of the formula (IX) are obtained analogously to Example (IX-1), such as, for example:

Example (IX-2)

Cl\C(CH₂F)(H₃C)₂C=CH—CHCl—C(CH₃)₂—CO—CH₂Br

Example (IX-3)

Cl\C(CH₂Cl)(H₃C)₂C=CH—CHCl—C(CH₃)₂—CO—CH₂Br

Starting substances of the formula (II)

Example (II-1)

Cl\(H₃C)₃C=CH—[cyclopropane with H₃C, CH₃, COOH]   Z—cis/trans 26.2 g of 1-bromo-4,6-dichloro-3,3,7,7-tetramethyl-5-octen-2-one in 50 ml of dioxane are added dropwise to a mixture of 31.75 g (0.793 mole) of sodium hydroxide in 286 ml of water and 30 ml of dioxane. The mixture is subsequently stirred at 20° C. for 10 hours and is diluted with water and extracted three times with methylene chloride. The aqueous phase is acidified with concentrated hydrochloric acid and extracted again three times with methylene chloride.

The acid extracts are combined, dried over sodium sulphate and evaporated.

3-(Z-2-Chloro-3,3-dimethyl-1-butenyl)-2,2-dimethyl-cyclopropane-1-carboxylic acid remains as an oil (cis:trans mixture about 35:65), which slowly starts to crystallize.

Example (II-2)

Cl\(H₃C)₂C=CH—[cyclopropane with H₃C, CH₃, COOH]   Z—trans 10 g of crude 1-bromo-4,6-dichloro-3,3,7,7-tetramethyl-5-octen-2-one (Example (IX-1)) are added dropwise to a solution of 88% pure powdered, technical grade potassium hydroxide in methanol (60.6 ml of 3N solution) at 50° C. After 15 minutes, the mixture is cooled and is subsequently stirred at 20° C. for a further 8 hours. It is then diluted with water and extracted three times with methylene chloride. The aqueous phase is acidified with concentrated hydrochloric acid and extracted again three times with methylene chloride. The organic phases are combined, dried over sodium sulphate and concentrated.

After trituration with petroleum ether, trans-3-(Z-2-chloro-3,3-dimethyl-1-butenyl)-2,2-dimethyl-cyclopropane-1-carboxylic acid of melting point M.p. 135° C. are obtained.

The remaining compounds of the formula (II) are prepared analogously to Example (II-1) and (II-2), such as, for example:

Example (II-3)

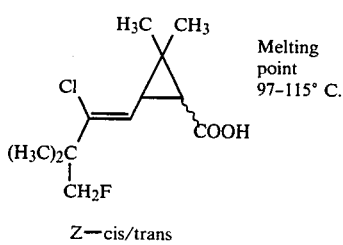

Melting point 97–115° C.

Z—cis/trans

Example (II-4)

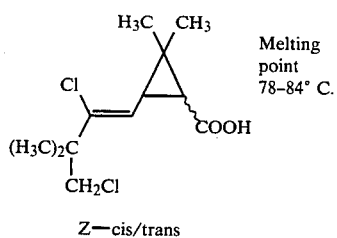

Melting point 78–84° C.

Z—cis/trans

Example (II-5)

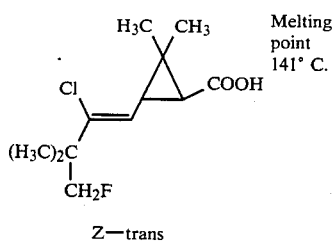

Melting point 141° C.

Z—trans

Starting substances of the formula (IIa)

Example (IIa-1)

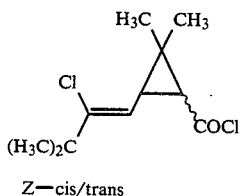

Z—cis/trans 38.9 g (0.168 mole) of cis/trans-3-(Z-2-chloro-3,3-dimethyl-1-butenyl)-2,2-dimethyl-cyclopropane-1-carboxylic acid are dissolved in 380 ml of carbon tetrachloride, and 30.2 g (0.253 mole) of thionyl chloride are added dropwise. The mixture is then heated under reflux for 4 hours and concentrated.

45.4 g of crude product are obtained, and are purified by distillation under a high vacuum (bulb tube).

The yield is 36.25 g (75.5% of theory) of cis/trans-3-(Z-2-chloro-3,3-dimethyl-1-butenyl)-2,2-dimethylcyclopropane-1-carboxylic acid chloride of boiling point B.p. 90° C./0.1 mbar.

The remaining compounds of the formula (IIa) are obtained analogously to Example (IIa-1).

Example A

Heliothis armigera test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soy bean shoots (Glycine max) are treated by being dipped into the preparation of the active compound of the desired concentration and are infested with tobacco budworm (Heliothis armigera), as long as the leaves are still moist.

After the specified periods of time, the destruction in % is determined. 100% means that all the worms have been killed; 0% means that none of the worms have been killed.

In this test, for example, the following compounds from the preparation examples show a superior activity compared to the prior art: (1) and (2).

Example B

Tetranychus test (resistant)

Solvent: 3 parts by weight of acetone
Emulsifier: 1 parts by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are heavily infested with the common spider mite or two-spotted spider mite (Tetranychus urticae) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example, the following compounds from the preparation examples show a superior activity compared to the prior art: (1), (6), (7) and (9).

Example C

Test insects: Phorbia antiqua maggots in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of the active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show a superior action compared to the prior art: (1), (2), (5), (6) and (8).

Example D

Test with *Boophilus microplus* resistant

Solvent:
35 parts by weight of ethylene glycol monomethyl ether
35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

10 adult Boophilus microplus res. are immersed for 1 minute in the active compound preparation to be tested. After transfer to plastic beakers and storage in a climatically controlled chamber, the degree of destruction is determined.

In this test, for example, the following compounds from the preparation examples show a superior activity compared to the prior art: (1), (2), (5), (6), and (9).

Example E

Test with *Lucilia cuprina* res. larvae

Emulsifier:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 Lucilia cuprina res. larvae are introduced into a test tube which contains about 1 cm² of horse meat and 0.5 ml of the preparation of active compound. After 24 hours, the degree of destruction is determined.

In this test, for example, the following compounds from the preparation examples show a superior action compared to the prior art: (1), (2) and (9).

It will be appreciated that the instant specification and examples are set forth by way of illustration and not limitation, and that various modifications and changes may be made without departing from the spirit and scope of the present invention.

We claim:
1. A 2,2-dimethyl-3-(2-halogenovinyl)-cyclopropane-carboxylic acid ester of the formula

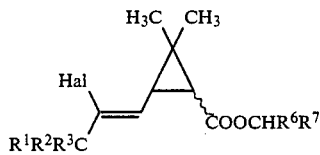

in which
$R^1$ and $R^2$ are identical or different and represent alkyl or halogenoalkyl,
$R^3$ represents alkyl or the grouping —(CH$_2$)—$_n$R$^4$,
in which
n represent 0 or 1 and
$R^4$ represents halogenoalkyl, optionally substituted aryl or the grouping —XR$^5$,
in which
X represents oxygen or sulphur and
$R^5$ represents alkyl, halogenoalkyl, optionally substituted aryl or optionally substituted aralkyl,
Hal represents fluorine, chlorine or bromine,
$R^6$ represents hydrogen, cyano or optionally substituted alkenyl or alkinyl with 2 to 4 carbon atoms and
$R^7$ represents phenyl or 2-pyridinyl, each of which is optionally substituted by halogen and/or phenoxy which is substituted by halogen, alkyl or halogenoalkyl.

2. A compound according to claim 1, in which
$R^1$ and $R^2$ are identical or different and represent alkyl with 1 to 6 carbon atoms or halogenoalkyl with 1 to 4 carbon atoms in the alkyl part and 1 to 5 identical or different halogen atoms, such as fluorine, chlorine and/or bromine,
$R^3$ represents alkyl with 1 to 12 carbon atoms or the grouping —(CH$_2$)$_n$R$^4$,
in which
$R^4$ represents halogenoalkyl with 1 to 4 carbon atoms in the alkyl part and 1 to 5 identical or different halogen atoms, optionally substituted aryl with 6 to 10 carbon atoms, or the grouping —X—R$^5$,
in which
$R^5$ represents alkyl with 1 to 6 carbon atoms, halogenoalkyl with 1 to 4 carbon atoms and 1 to 5 identical or different halogen atoms, or aryl which has 6 to 10 carbon atoms and aralkyl which has 6 to 10 carbon atoms in the aryl part and 1 or 2 carbon atoms in the alkyl part and is optionally substituted by alkyl, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms and/or halogen, such as fluorine, chlorine and/or bromine, and
Hal represents fluorine, chlorine or bromine.

3. A compound according to claim 1, in which
$R^1$ and $R^2$ are identical or different and represent alkyl with 1 to 4 carbon atoms or halogenoalkyl with 1 or 2 carbon atoms in the alkyl part and 1 to 3 identical or different halogen atoms,
$R^3$ represents alkyl with 1 to 6 carbon atoms or the grouping —(CH$_2$)$_n$R$^4$,
in which
$R^4$ represents halogenoalkyl with 1 to 4 carbon atoms in the alkyl part and 1 to 5 identical or different halogen atoms, optionally substituted phenyl or the grouping —X—R$^5$,
in which
$R^5$ represents alkyl with 1 to 4 carbon atoms, halogenoalkyl with 1 to 4 carbon atoms and 1 to 5 identical or different halogen atoms, or phenyl or phenylalkyl, with 1 or 2 carbon atoms in the alkyl part, which is optionally substituted by fluorine, chlorine, methyl, tert.-butyl, methoxy, methylthio, trifluoromethyl and/or trifluoromethoxy,
Hal represents chlorine or bromine,
$R^6$ represents hydrogen or cyano and
$R^7$ represents 3-phenoxy-phenyl, 4-fluoro-3-phenoxyphenyl, 3-(4-fluoro-phenoxy)-phenyl, 4-fluoro-3-

(4-fluoro-phenoxy)-phenyl, pentafluorophenyl or 6-phenoxy-2-pyridyl.

4. A compound according to claim 1, in which $R^1$ and $R^2$ are identical or different and represent methyl, ethyl, chloromethyl, chloroethyl, fluoromethyl or fluoroethyl, $R^3$ represents methyl, ethyl, n-propyl, impropyl, n-butyl, n-pentyl, n-hexyl or the grouping $-(CH_2)_nR^4$, in which $R^4$ represents chloromethyl, fluoromethyl, phenyl which is optionally substituted by fluorine, chlorine, bromine, methyl, methoxy, trifluoromethyl or trifluoromethoxy, or the grouping $XR^5$, in which $R^5$ represents methyl, ethyl, trifluoromethyl, trichloromethyl, or phenyl or benzyl which is optionally substituted by fluorine, chlorine, bromine, methyl, methoxy, trifluoromethyl and/or trifluoromethoxy, Hal represents chlorine, $R^6$ represents hydrogen or cyano and $R^7$ represents 3-phenoxy-phenyl, 4-fluoro-3-phenoxy-phenyl or pentafluorophenyl.

5. A compound according to claim 1, in which $CHR^6R^7$ is the radical of an alcohol selected from the group consisting of 6-phenoxy-2-pyridyl methanol, α-cyano-6-phenoxy-2-pyridylmethanol, 4-fluoro-3-phenoxy-benzyl alcohol, 3-phenoxy-benzyl alcohol, α-cyano-4-fluoro-3-phenoxybenzyl alcohol, α-cyano-3-phenoxy-benzyl alcohol, 4-fluoro-3-(4-chloro-phenoxy)-benzyl alcohol, 4-fluoro-3-(4-bromo-phenoxy)-benzyl alcohol, pentafluoro benzyl alcohol, 4-fluoro-3-(4-fluoro-phenoxy)-benzyl alcohol, α-cyano-4-fluoro-3-(4-fluoro-phenoxy)-benzyl alcohol, 4-fluoro-3-(3-fluoro-phenoxy)-benzyl alcohol and α-cyano-4-fluoro-3-(3-fluoro-phenoxy)-benzyl alcohol.

6. A compound according to claim 1, wherein such compound is α-cyano-4-fluoro-3-phenoxy-benzyl 3-(2-chloro-3,3-dimethyl-1-butenyl)-2,2-dimethyl-cyclopropane-1-carboxylate of the formula

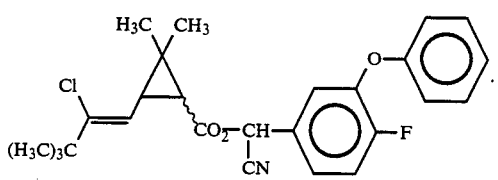

7. A compound according to claim 1, wherein such compound is α-cyano-3-phenoxy-benzyl 3-(2-chloro-3,3-dimethyl-1-butenyl)-2,2-dimethyl-cyclopropane-1-carboxylate of the formula

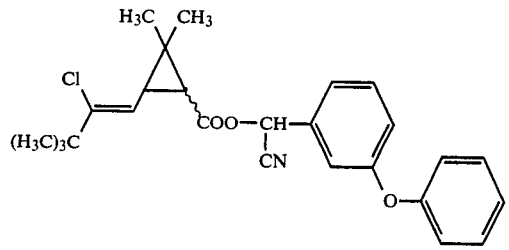

8. A compound according to claim 1, wherein such compound is α-cyano-4-fluoro-3-phenoxy-benzyl 3-(2-chloro-3,3-dimethyl-4-fluoro-1-butenyl)-2,2-dimethyl-cyclopropane-1-carboxylate of the formula

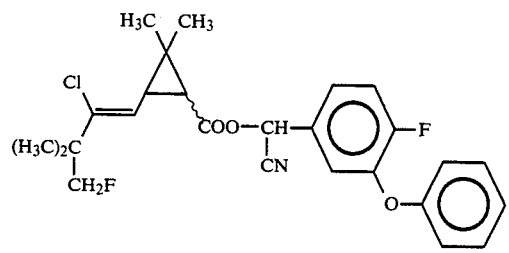

9. A compound according to claim 6, wherein the carboxylate is Z trans.

10. A compound according to claim 8, wherein the carboxylate is Z trans.

11. An insecticidal and acaricidal composition comprising an insecticidally and acaricidally effective amount of a compound according to claim 1 in admixture with a diluent.

12. A method of combating insects and acarids which comprises administering to such insects and acarids or a habitat thereof an insecticidally and acaricidally effective amount of a compound according to claim 1.

13. The method according to claim 12, wherein such compound is

α-cyano-4-fluoro-3-phenoxy-benzyl 3-(2-chloro-3,3-dimethyl-1-butenyl)-2,2-dimethyl-cyclopropane-1-carboxylate, α-cyano-3-phenoxy-benzyl 3-(2-chloro-3,3-dimethyl-1-butenyl)-2,2-dimethyl-cyclopropane-1-carboxylate or α-cyano-4-fluoro-3-phenoxy-benzyl 3-(2-chloro-3,3-dimethyl-4-fluoro-1-butenyl)-2,2-dimethyl-cyclopropane-1-carboxylate.

14. A 2,2-dimethyl-3-(2-halogenovinyl)-cyclopropanecarboxylic acid or derivative thereof of the formula

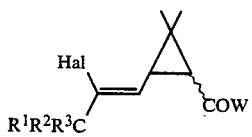

in which $R^1$ and $R^2$ are identical or different and represent alkyl or halogenoalkyl, $R^3$ represents alkyl or the grouping $-(CH_2)-_nR^4$, in which n represents 0 or 1 and $R^4$ represents halogenoalkyl, optionally substituted aryl or the grouping $-XR^5$, in which X represents oxygen or sulphur and $R^5$ represents alkyl, halogenoalkyl, optionally substituted aryl or optionally substituted aralkyl, Hal represents fluorine, chlorine or bromine and W represents OH, halogen or $C_1$-$C_4$-alkoxy.

* * * * *